United States Patent [19]

Nirschl

[11] 4,441,493

[45] Apr. 10, 1984

[54] ELBOW BRACE

[76] Inventor: Robert P. Nirschl, 4143 N. River St., Arlington, Va. 22207

[21] Appl. No.: 422,349

[22] Filed: Sep. 23, 1982

[51] Int. Cl.³ .......................................... A61F 13/00
[52] U.S. Cl. .................................................. 128/165
[58] Field of Search ................ 128/165, 77, 169, 157; 273/189 R, 189 A, 291

[56] References Cited

U.S. PATENT DOCUMENTS

| | | | |
|---|---|---|---|
| 3,789,842 | 2/1974 | Froimson | 128/165 |
| 3,877,426 | 4/1975 | Nirschl | 128/165 |
| 4,182,318 | 1/1980 | Beige et al. | 128/77 |
| 4,299,214 | 11/1981 | Sweitzer | 128/165 |

Primary Examiner—John D. Yasko
Attorney, Agent, or Firm—Staas & Halsey

[57] ABSTRACT

A brace for supporting the tendons of the human elbows comprised of a flexible, curvilinear pad having a substantially triangular projection extending therefrom and a rigid, angled reinforcing member positioned centrally of the projection for applying pressure to the medial epicondyle. The brace is of substantial width especially adapted to be tightly wrapped about the upper forearm and elbow without slippage and is constructed of a two-layer laminate of cloth and foam rubber, or like resilient materials. The pad is easily tightened about the upper forearm by means of Velcro fastener strips attached thereon, and the projection is further secured to the elbow by an elastic strap which crosses the upper arm at the elbow joint and attaches to both sides of the projection. The elastic strap also increases the pressure exerted by the projection over the medial epicondyle.

12 Claims, 4 Drawing Figures

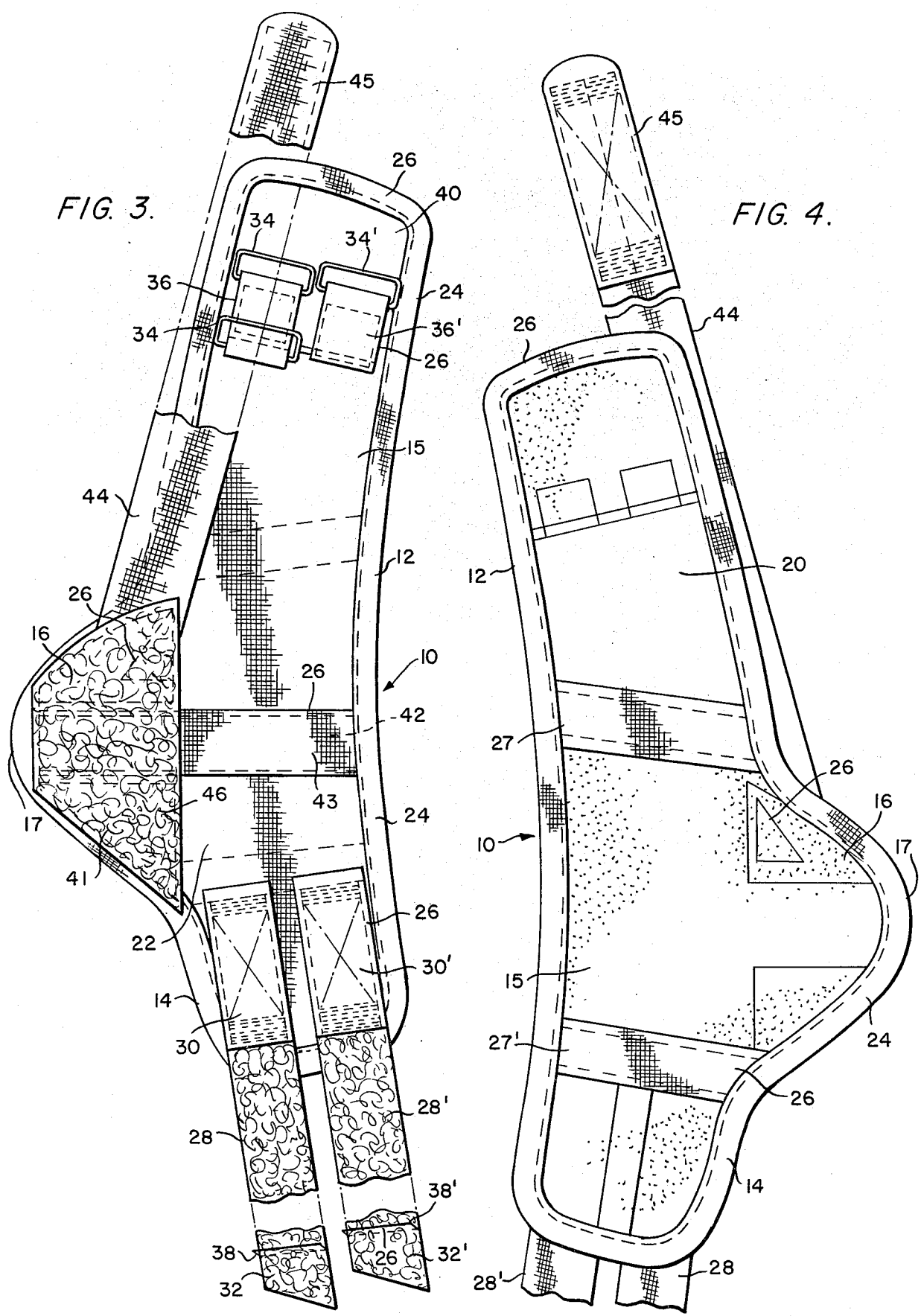

ELBOW BRACE

BACKGROUND OF THE INVENTION

1. Field of the Invention

This invention pertains to a brace for supporting the musculo-tendinous units in the human elbow. In particular, this invention relates to a brace for relieving the injury known as tennis elbow, which is a painful inflamation of the tendon attachments at the prominence of the elbow, by applying external pressure over a wide area of the elbow.

2. Description of the Prior Art

The increasing popularity of tennis has brought with it a new musculo-tendinous injury called "tennis elbow". The term tennis elbow often inaccurately includes many injuries and discomforts which occur in and about the elbow. The primary symptom of tennis elbow is a painful chronic inflamation of the attachment of the tendons at the elbow epicondyles. This can occur at either the medial or lateral elbow epicondyles. For the most part, the problem occurs because of an inherent weakness in the design or mechanical relationship of the musculo-tendinous of the arm, which subject the elbow to increased forces in a specific area placing an inordinate strain on these tissues.

It has been found that the pain of tennis elbow can be relieved and the injury itself often prevented by placing pressure about the elbow. For example, a bandage-like device called the Froimson tennis elbow support, disclosed in U.S. Pat. No. 3,789,842, teaches a support for wrapping about the smaller muscle of the forearm just below the elbow joint. This device seeks to relieve discomfort by resisting expansion of the forearm.

Another elbow support design is disclosed in U.S. Pat. No. 4,299,214, issued to Sweitzer. This patent discloses a semirigid sleeve having a pressure pad formed in the wall of the sleeve positioned to apply pressure over the proximal extensor or flexor muscle group on the lateral or medial side of the proximal forearm, respectively.

Finally, my earlier muscular support, disclosed in U.S. Pat. No. 3,877,426, teaches an arcuately-shaped elongated pad, which approximates a cone when wrapped about the forearm of the wearer. In addition, two straps having Velcro fasteners are used to secure the support around the wearer's limb.

Each of the above-mentioned devices does not adequately alleviate the injury and subsequent discomfort of tennis elbow because of one or more of the following reasons: (1) the devices are difficult for the tennis player to apply and adjust, if unassisted; (2) the devices have a tendency to slip from their proper positions on the arm during physical activity (e.g., a tennis game); (3) the devices are inconvenient and uncomfortable to wear during daily activities; (4) the devices often pinch nerves and blood vessels; and, most importantly, (5) these devices do not apply pressure to the pathological areas of the arm to gain optimum support and relief where needed, i.e., on both the medial and lateral upper forearm tendons which connect to the elbow.

Thus, it can be seen that the prior art brace devices for alleviating tennis elbow still have inherent disadvantages. None of the known prior art devices has the novel features of the invention disclosed herein for eliminating these disadvantages while maintaining a low-cost, easily manufactured brace.

OBJECTS OF THE INVENTION

In light of the above-mentioned disadvantages in the prior art elbow braces, it is an object of this invention to provide an elbow brace which can be wrapped about the elbow and upper forearm and properly adjusted without assistance from a second person.

It is another object of this invention to provide an elbow brace that is slightly curvilinear in design and assumes a generally conical shape of the elbow and upper forearm about which it is wrapped.

It is still another object of this invention to provide an elbow brace resisting slippage from the elbow and upper forearm during vigorous athletic motion such as that occuring during a game of tennis.

It is another object of the present invention to provide an elbow brace which is adjustable, flexible and non-cumbersome, thus ensuring convenient and comfortable wear during daily activities.

It is yet another object of the present invention to provide an elbow brace which applies pressure at both the medial and lateral upper forearm muscles and elbow tendons, thus ensuring optimum support for the elbow to prevent or relieve both medial and lateral tennis elbow.

Finally, it is another object of this invention to provide a brace using a strong pad of rugged, long wearing characteristics, which is relatively easily and inexpensively manufactured and which maintains its appearance and utility over lengthy use.

SUMMARY OF THE INVENTION

These and other objects of the invention are achieved by an elbow brace comprising a flexible, arcuately-shaped pad having a main body and a substantially triangular projection extending therefrom, which together contour the forearm as well as support the forearm tendons connected to the elbow. The main body has a length greater than its width and is shaped to approximate the frustrum of a cone when wrapped about the upper forearm. One end of the main body has two Velcro fastener strips attached to the outer surface of the outer layer and the other end of the main body has two rings attached to the outer surface of the other side. Each Velcro fastener strip has a loop section and a hook section, and one of the sections of each Velcro strip partially overlaps the main body, while the other of the sections comprising a free end. The main body of the brace can be fastened around the upper forearm by threading the free end of each strip throuqh the respective rings and reversedly drawing said free ends for attachment to the other sections of the Velcro fasteners, thereby tightening the support device around the upper forearm. The substantially triangular projection extending from the main body is adapted to be positioned over the medial epicondyle of the elbow. An angled metal reinforcing member is partially positioned within the main body parallel to the forearm and extends into the substantially triangular projection to contour the medial epicondyle, and an adjustable elastic strap encircles the upper arm above the joint and is attached to both sides of the projection. The adjustable elastic strap functions to increase the pressure exerted by the projection over the medial epicondyle or olecranon. Alternatively, the elbow brace may be worn such that the projection is positioned over the lateral epicondyle or olecranon.

When the elbow brace is in place, the projection, the adjustable elastic strap and the reinforcing member, in combination with the main body secured to the upper forearm by the Velcro strips, satisfy the objects set out above. More particularly, the uniquely curved and angled brace exerts adequate pressure to the upper forearm and elbow tendons to provide optimum support for these areas and thus, help prevent or alleviate the symptoms of tennis elbow.

BRIEF DESCRIPTION OF THE DRAWINGS

These and other objects and advantages of the invention will become more apparent to those skilled in the art by reference to the following drawings:

FIG. 3 is a top plan view of the elbow brace of the present invention; and

FIG. 4 is a bottom plan view of the elbow brace of the present invention.

DETAILED DESCRIPTION OF THE PREFERRED EMBODIMENTS

Figure 2:
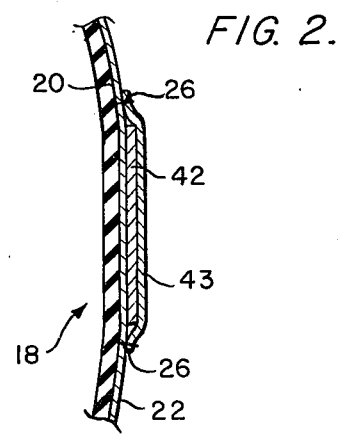
FIG. 2 is a cross-sectional view of the elbow brace, as shown in FIG. 1, taken along line 2—2, illustrating particularly the location of the reinforcing member.

As best seen in FIGS. 2 and 3, the elbow brace of the preferred embodiment of the present invention comprises a substantially curvilinear, elongated pad 10 having one convexly arcuately-shaped long edge 12 and having an opposing long edge 14 with a portion thereof non-parallel to edge 12. The pad 10 has two portions: a main body portion 15 defined substantially by the edges 12 and 14, and a substantially triangular projection 16 extending away from the convexly arcuately-shaped long edge 12.

Figure 1:
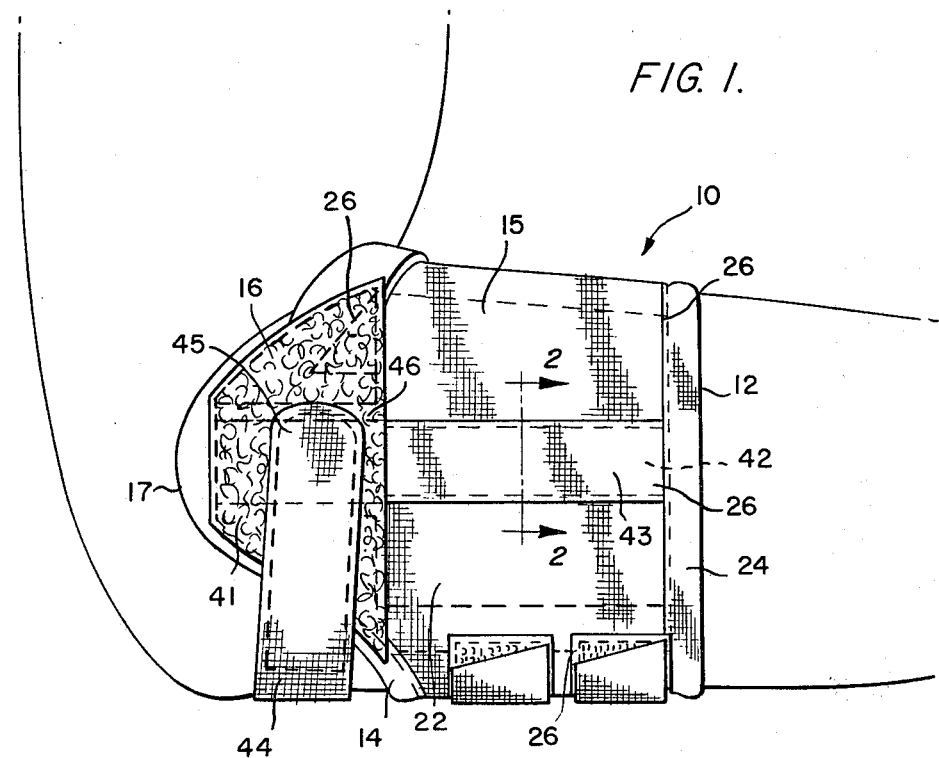
FIG. 1 is a side view of the elbow brace of the present invention in position, tightly wrapped about the medial area of the left elbow of a wearer, as viewed from the inside of the elbow.

The convexly arcuately-shaped long edge 12 is of a greater length, measured longitudinally of the elongated pad 10, than the opposing long edge 14 such that the elbow brace will assume a generally conical shape when wrapped about the upper forearm and elbow, as illustrated in FIG. 1. This configuration provides for support by the exertion of an even pressure around the upper forearm and particular pressure on the medial epicondyle; thus the pad extends over a wide area but it does not significantly impair movement of the arm. Additionally, the conical configuration of the brace aids in preventing slippage and displacement of the device during athletic exertion.

As best seen in FIG. 2, pad 10 comprises a laminate 18 with one of the layers being a polymeric foam bottom layer 20, which is preferably foam rubber of about one-eighth inch to one-fourth inch thickness. Extra padding is used at the central portion of the main body 15 and the projection 16.

A suitable laminate of foam rubber and cotton is commercially available from PROTEK-TOE PRODUCTS, of Union, N.J. It is possible to use other foams than foam rubber, but the foam should be selected so that it is highly resilient, has similar "fight back" properties so it tends to resist compression, and has a coefficient of friction sufficiently similar to that of foam rubber, whereby it resists slipping even when the skin underneath the support device begins to sweat. Preferably, the surface of the foam rubber is smooth appearing and the pore size of the foam at the surface is very tiny, giving the outer surface of the foam a skin-like appearance.

The laminate 18 is also comprised of a top layer 22, which is a relatively inelastic sheet, preferably cotton duck cloth. The top layer 22 is relatively inelastic because inelastic material minimizes circulatory blockage, such as is present with the use of the elastic wrappings and supports known in the prior art.

When the pad 10 is wrapped about the forearm and elbow, the bottom layer 20 and the top layer 22 are the inner and outer layers, respectively, of the elbow brace.

The laminate 18 is preferably bordered by a binding strip 24, which is an elasticized fabric. The elastic binding strip 24 is sewn on, as are all other attachments to the pad 10, by stitching 26 which is sewn through the foam rubber side. By sewing through the foam rubber side is meant stitching with the foam rubber side in the upper position, the stitches 26 causing the bottom foam rubber layer 20 to compress. The stitches, therefore, are indented below the surface that is in contact with the skin, thereby lessening the danger of skin irritation due to abrasion caused by raised stitching.

There is also provided on the bottom layer 20 of the pad 10, relatively inelastic cloth strips 27 and 27', which are located substantially perpendicularly to the edges 12 and 14 of the pad 10, to either side below the projection 16. These strips 27 and 27' aid in providing additional structural integrity to the main body 15, and also effectively act as hinges to aid in bending the pad 10 around the upper forearm and elbow.

To one end of the pad 10 is attached a pair of flexible Velcro or equivalent fastener strips 28 and 28' for attaching the main body 15 to the elbow of the wearer. Each fastener strip has hooked portions 30 and 30' and loop portions 32 and 32'. The other end of the pad has several rigid metal rings 34 and 34' attached to the flexible outer sheet layer 22 by looped cloth ribbons 36 and 36'.

The brace is kept firmly about the elbow by threading the free loop ends 32 and 32' of Velcro fastener strips 28 and 28' through the underside of rigid metal rings 34 and 34' and reversedly back for attachment to the hook ends 30 and 30' of the Velcro fastener strips 28 and 28'.

Conveniently, the free ends 32 and 32' of the Velcro fastener strips can be looped back upon themselves and stitched, thereby forming raised portions or catches 38 and 38' which are adapted to engage the metal rings 34 and 34'. These raised portions 38 and 38' thus permit the user to form a circular, loosely engaged support through which he can insert his arm prior to final positioning of the support device about the forearm and elbow and tightening of the Velcro fastener strips 28 and 28'.

To facilitate tightening and prevent misalignment of the ends of the pad when the fastener strips 28 and 28' are tightly drawn, a particularly preferred embodiment shown in FIG. 3 has a plastic sheet material 40, such as celluloid or its equivalent, stitched onto the upper surface of the upper layer 22 below the metal rings 34 and 34'.

As shown more clearly in FIG. 1, the projection 16 of the elbow brace extends from edge 14 and is designed to accommodate the medial epicondyle in the preferred embodiment. The projection is widest at the area it meets the main body 15, i.e., the base 46, and tapers to form a rounded end 17 in the vicinity of the medial epicondyle. The entire projection 16 is covered on the top layer 22 with a looped-cloth area 41 for joining with the Velcro-hooked end of an elastic strap 44, which will be described hereafter. This configuration ensures that the brace is capable of covering the entire medial epicondyle and its immediate area for adequate support of the medial epicondyle.

As best seen in FIGS. 1, 2 and 3, reinforcing member 42, which is a rigid strip of, e.g., metal or synthetic resin, provides additional stabilizing strength for the medial epicondyle. The reinforcing member 42 is partially positioned within the main body 15 of the pad 10 parallel to the forearm, extends into the projection 16 and is angled to contour the medial epicondyle. The reinforcing member is enclosed by an inelastic rectangular cloth strip 43 sewn to the outer layer 22 of the pad 10.

The reinforcing member 42 can be bent by the user as preferred to exert different amounts of pressure upon the medial epicondyle. Basically, the user should bend the reinforcing member 42 about two inches interior of the end 17 of the projection 16. As stated, bending the reinforcing member 42 increases the pressure upon and support of the Achilles tendon. Preferably, the reinforcing member 42 is bent at the end farthest away from edge 12 to an angle of about 10 degrees toward the elbow.

An elastic strap 44 is also provided stitched to one side of the projection 16. The strap 44 has a free end 45 covered on one side by Velcro hooked material for fastening to the Velcro looped area 41 on the top layer of the projection 16. The elastic strap 44 extends from one side of the projection 16 where it is stitched at the base 46, across the upper arm at the elbow joint, and reattaches, as stated, by the use of the free end 45 with the Velcro hooked material of the Velcro looped area 41 of the projection 16.

This fastening configuration provides adequate adjustment of the strap 44 on the projection 16. The elastic strap 44 is intended to firmly hold the medial epicondylar extension down against the pathological area of the medial epicondyle.

To summarize application of the brace to the elbow area, the wearer first inserts the free ends of Velcro fastener strips 28 and 28' through the rings 34 and 34', respectively, such that catches 38 and 38' are caught against the rings 34 an 34', thus generally prohibiting removal of the strips 28 and 28' from the rings 34 and 34'. The brace should then be slipped over the forearm with the projection 16 preferably positioned over the medial elbow point. The strips 28 and 28' can then be adjusted and fastened to the Velro hooked portions 30 and 30'. Then, elastic strap 44 should be pulled across the area just above the elbow joint and reattached to the projection 16. Straps 28 and 28', and strap 44, should be adjusted so that the wearer feels comfortably snug pressure on the medial point of the elbow.

It has been found that convenient dimensions for this elbow brace are in the range of 2 to 4 inches between the base 46 of the projection 16 and the convexly arcuately-shaped long edge 12, 1½ to 3½ inches for between the base of the projection 46 and the rounded end 17 of the projection 16, and 10 to 15 inches measured linearly longitudinally along the main body 15 of the pad 10. Size of the elbow brace is not important but it is advantageous to have several sizes, each sufficient to be wrapped about and completely surround the elbow and forearm without extensive overlap.

When the brace of this embodiment is firmly fastened about the forearm and elbow, as shown in FIG. 1, it provides pressure about the upper forearm, and especially against the medial epicondyle, and thus disseminates any excessive concentration of forces at and about the elbow during athletic exertion. This brace is configured to avoid immobilizing the elbow joint of the wearer and thus avoids hinderance of the wearer's athletic activities while still providing musculo-tendinous support over a broad area.

Alternatively, this brace may also be applied over the upper forearm and elbow such that the projection 16 is positioned over the lateral epicondyle or over the olecranon area. Thus, the reinforcing member would then be applying pressure to the lateral epicondyle or posterior triceps to prevent or alleviate symptoms of tennis elbow in these areas. All other features and means for attaching and adjusting the brace as described for the preferred embodiment, are equally applicable to this alternate embodiment.

The brace of the invention can be used for the prevention of other injuries and alleviation of the pain associated with these injuries; e.g., by those who work at occupations such as carpentry which, because of their nature, cause injuries similar to those caused by sports.

While the preferred embodiment of the brace of this invention, which is especially suited for the disclosed specialized applications, has been disclosed with particularity above, numerous modifications of the same within the scope of the art. Additionally, various configurational modifications of the brace of this device to facilitate application of the invention to the elbow, will occur to those skilled in the art and are considered also to be encompassed by this invention. Thus, the scope of the invention of this elbow brace is to be limited solely by the claims appended hereto.

I claim:

1. A brace device capable of being wrapped about the elbow and forearm and capable of applying pressure to a wide area of the elbow to thereby relieve internal musculo-tendonous tension about the elbow, comprising: a substantially curvilinear, elongated pad of a generally conical shape when wrapped about the elbow and forearm, the pad being substantially flexible in all directions and having a laminate with an inner layer of resilient foamed material bonded to an outer layer of substantially inelastic flexible sheet, the pad further having a main body, a substantially triangular projection extending therefrom, and fastening means for securing the support device tightly about the elbow and forearm; the main body having one long edge convexly arcuately-shaped, an opposing long edge, a first end and a second end; and the projection extending away from the main body and having a rigid reinforcing member extending parallel to the forearm along the projection and into the main body.

2. The brace according to claim 1, wherein the fastening means comprise at least one Velcro fastener strip attached to the outer surface of the outer layer at the first end of the elongated pad for attachment to the second end.

3. The brace according to claim 1, wherein the fastening means comprise an elastic strap which extends from one side of the substantially triangular projection, around the upper arm at the elbow joint, and reattaches to the other side of the projection.

4. The brace of claim 1, wherein said fastening means comprise:

(a) a plurality of Velcro fastener strips attached to the outer surface of the outer layer at the first end of the elongated pad, a corresponding plurality of rings attached to the outer surface of the outer layer at the second end of the pad, each Velcro fastener strip having a loop section and a hook section, one end of each Velcro fastener strip partially overlapping the pad and the other end of each fastener strip constituting a free end, whereby the pad can be fastened around the forearm by threading each free end of each strip through the corresponding ring and reversedly drawing the free end for attachment to the corresponding overlapping section; and (b) an elastic strap which extends from one side of the substantially triangular projection, around the upper arm at the elbow joint, and reattaches to the projection.

5. The brace of claim 1, 2, 3, or 4, wherein the reinforcing member comprises: a relatively stiff elongated strip of a substantially rigid synthetic resin.

6. The brace of claim 5, wherein the reinforcing member has one end bent at an angle.

7. The brace of claim 1, 2, 3 or 4, wherein the reinforcing member comprises a metal elongated strip.

8. The brace of claim 7, wherein the reinforcing member has one end bent at an angle.

9. The brace of claim 6, wherein the reinforcing member is angled at approximately 10 degrees.

10. The brace of claim 1, wherein the resilient foamed material is foam rubber.

11. The brace of claim 1, wherein the substantially inelastic flexible sheet is a woven fabric.

12. The brace of claim 8, wherein the reinforcing member is angled at approximately 10 degrees.

* * * * *

UNITED STATES PATENT AND TRADEMARK OFFICE
CERTIFICATE OF CORRECTION

PATENT NO. : 4,441,493

DATED : 4/10/84

INVENTOR(S) : Robert P. Nirschl

It is certified that error appears in the above-identified patent and that said Letters Patent is hereby corrected as shown below:

Col. 2

Line 50, "throuqh" should be --through--.

Col. 6

Line 32, after "is" insert --not--.

Signed and Sealed this

Fourth Day of September 1984

[SEAL]

Attest:

GERALD J. MOSSINGHOFF

Attesting Officer    Commissioner of Patents and Trademarks